US007285363B2

(12) United States Patent
Campagnola et al.

(10) Patent No.: US 7,285,363 B2
(45) Date of Patent: Oct. 23, 2007

(54) PHOTOACTIVATORS, METHODS OF USE, AND THE ARTICLES DERIVED THEREFROM

(75) Inventors: Paul J. Campagnola, Simsbury, CT (US); Amy R. Howell, Tolland, CT (US); Jun Wang, Audubon, PA (US); Steven L. Goodman, Madison, WI (US)

(73) Assignee: The University of Connecticut, Storrs, CT (US)

( * ) Notice: Subject to any disclaimer, the term of this patent is extended or adjusted under 35 U.S.C. 154(b) by 0 days.

(21) Appl. No.: 10/705,254

(22) Filed: Nov. 10, 2003

(65) Prior Publication Data

US 2004/0259023 A1    Dec. 23, 2004

(51) Int. Cl.
  *G03F 7/012*    (2006.01)
  *G03C 9/08*    (2006.01)
  *G03C 1/76*    (2006.01)
(52) U.S. Cl. .................... 430/8; 430/11; 430/194; 430/195; 430/197; 430/269; 430/270.1
(58) Field of Classification Search .................. 430/8, 430/194, 195, 196, 197
  See application file for complete search history.

(56) References Cited

U.S. PATENT DOCUMENTS

| | | | | |
|---|---|---|---|---|
| 3,265,772 A | * | 8/1966 | Tocker | 522/109 |
| 3,594,348 A | * | 7/1971 | Maar et al. | 526/62 |
| 4,131,466 A | * | 12/1978 | Nomura et al. | 430/270.1 |
| 4,197,133 A | * | 4/1980 | Zweifel et al. | 430/197 |
| 4,424,325 A | * | 1/1984 | Tsunoda et al. | 430/195 |
| 4,433,043 A | * | 2/1984 | Sawada et al. | 430/175 |
| 4,503,140 A | * | 3/1985 | Wright | 430/289.1 |
| 4,602,097 A | * | 7/1986 | Curtis | 522/36 |
| 5,289,407 A | | 2/1994 | Strickler et al. | |
| 5,518,864 A | * | 5/1996 | Oba et al. | 430/325 |
| 5,637,460 A | * | 6/1997 | Swan et al. | 435/6 |
| 5,714,360 A | * | 2/1998 | Swan et al. | 435/174 |
| 5,912,257 A | | 6/1999 | Prasad et al. | |
| 6,008,265 A | * | 12/1999 | Vallee et al. | 522/25 |
| 6,048,660 A | * | 4/2000 | Leppard et al. | 430/270.1 |
| 6,267,913 B1 | | 7/2001 | Marder et al. | |
| 6,300,502 B1 | | 10/2001 | Kannan et al. | |

(Continued)

FOREIGN PATENT DOCUMENTS

WO    WO-93/16131 A1 *    8/1993

(Continued)

OTHER PUBLICATIONS

Yang et al SPIE vol. 469 Advances in Resist Technology (1984) pp. 117-126.*

(Continued)

*Primary Examiner*—Cynthia Hamilton
(74) *Attorney, Agent, or Firm*—Cantor Colburn LLP

(57) ABSTRACT

A method for crosslinking one or more molecules comprises crosslinking the one or more molecules with a photactivatable crosslinker by one-photon or multi-photon excitation, wherein the crosslinker comprises at least two photoactive groups linked by a bridging moiety, and further wherein the point volume of the activation has at least one dimension of less than about 1 micron. The method is of particular utility for water-soluble molecules, particularly biologically active water-soluble molecules.

15 Claims, 2 Drawing Sheets

U.S. PATENT DOCUMENTS

| | | | |
|---|---|---|---|
| 6,316,153 B1 | 11/2001 | Goodman et al. | |
| 6,706,408 B2* | 3/2004 | Jelle | 428/447 |
| 2002/0169107 A1* | 11/2002 | Rajagopalan et al. | 514/2 |
| 2003/0194715 A1* | 10/2003 | Li et al. | 435/6 |

FOREIGN PATENT DOCUMENTS

| | | | |
|---|---|---|---|
| WO | WO97/07161 A1 * | 2/1997 | |
| WO | WO-99/54784 A1 * | 10/1999 | |
| WO | WO 01/21326 A1 * | 3/2001 | |

OTHER PUBLICATIONS

Dean, J.A, ed,Lange's Handbook of Chemistry, 15th ed, Mc Graw-Hill, 1999, pp. 7.18-7.20.*

Hawley's Condensed Chemical Dictionary, 14th ed, 2002, John Wiley & Sons, inc,"chromophore" one page from internet site www.knovel.com.*

Rosato et al eds, Concise Encyclopedia of Plastics, Springer-Verlag, 2000, p. 381.*

Mikhant'eva et al, AN 1981:532432 entered into Sten May 12, 1984, Abstract, CAPLUS, ACS on STN.*

LEong, AN 1971:105633, entered STN May 12, 1984, Abstract, CAPLUS, ACS on STN.*

Vincent D. McGinniss, "Radiation Curing", pp. 1-25 from Kirk-Othmer Encyclopedia of Chemical Technology (posted online Dec. 4, 2000 on www.mrw.interscience.wiley.com, copyrighted by John Wiley & Sons, Inc in 1996.*

Thompson et al, eds , Introduction to Microlithography, Second Edition, ACS Professional Reference Book, American Chemical Society, Washington, DC 1994 pp. 162-165.*

Cao et al, "Synthesis of Diazoresin and its Photocrosslinking Reaction", Polymer International, vol. 45 , 1998, pp. 142-146, no month given.*

Agarwal, Rajesh, et al, "Identification Of The Site Of Photocrosslinking Formed In The Absence Of Magnesium Nucleotide From SH2 (Cys-697) In Myosin Subfragment 1 Labeled With 4'—Maleimidylbenzophenone", The Journal Of Biological Chemistry, vol. 266, No. 4 (1991) pp. 2272-2275.

Albota, Marius, et al, "Design of Organic Molecules With Large Two-Photon Absorption Cross Sections", Science, vol. 281 (1998) pp. 1653-1656.

Belfield, Kevin D., et al, "Near-IR Two-Photon Photoinitiated Polymerization Using A Fluorone/Amine Initiating System", Journal of American Chemical Society, vol. 122 (2000) pp. 1217-1218.

Bhawalkar, Ph.D., J.D., "Two-Photon Photodynamic Therapy", Journal of Clinical Laser Medicine & Surgery, vol. 15, No. 5 (1997) pp. 201-204.

Campagnola, Paul J., et al, "3-Dimensional Submicron Polymerization Of Acrylamide By Multiphoton Excitation Of Xanthene Dyes", Macromolecules, vol. 33, (2000) pp. 1511-1513.

Cheng, P.C., et al, "Two-Photon Generated Three-Dimensional Photo-Bleached Patterns in A Polymer Matrix", Scanning, vol. 18, (1996) pp. 129-131.

Cumpston, Brian H., et al, "Two-Photon Polymerication Initiators For Three-Dimensional Optical Data Storage And Microfabrication", Nature, vol. 398 (1999) pp. 51-54.

Day, Daniel, et al, "Use Of Two-Photon Excitation For Erasable-Rewritable Three-Dimensional Bit Optical Data Storage In A Photorefractive Polymer", Optics Letters, vol. 24, No. 14 (1999) pp. 948-950.

Denk, Winfried, et al, "Two-Photon Laser Scanning Fluorescence Microscopy", Science, vol. 248 (1990) pp. 73-76.

Fittinghoff, D.N., et al, "Time-Decorrelated Multifocal Array For Multiphoton Microscopy And Micromachining", Optics Letters, vol. 25, No. 16, (2000) pp. 1213-1215.

Gu, Min, et al, "Comparison Of Three-Dimensional Imaging Properties Between Two-Photon And Single-Photon Fluorescence Microscopy", Journal of Microscopy, vol. 177, (1995) pp. 128-137.

Hartwig, John F., "Palladium-Catalyzed Amination Of Aryl Halides: Mechanism And Rational Catalyst Design", Synlett, (1997) pp. 329-340.

Jackman, Rebecca J., et al, "Three-Dimensional Metallic Microstructures Fabricated By Soft Lithography And Microelectrodeposition", Langmuir, vol. 15, (1999) pp. 826-836.

Jackman, Rebecca J., et al, "Design And Fabrication Of Topologically Complex, Three-Dimensional Microstructures", Science, vol. 280, (1998) pp. 2089-2091.

James, C.D., et al, "Patterned Protein Layers On Solid Substrates By Thin Stamp Microcontact Printing", Langmuir, vol. 14, (1998) pp. 741-744.

Kawata, S., et al, "Finer Features For Functional Microdevices", Nature, vol. 412 (2001) pp. 697-698.

Konig, K, et al, "Cellular Response To Near-Infrared Femtosecond Laser Pulses In Two-Photon Microscopes", Optics Letters, vol. 22, No. 2, (1997) pp. 135-136.

Kuebler, Stephen M., et al, "Two-Photon Polymerization Initiators For Efficient Three-Dimensional Optical Data Storage And Microfabrication", Quantum Electronics and Laser Science Conference, (1999) pp. 52.

Ledger, M.B., et al, "Primary Photochemical Processes in Aromatic Molecules", Journal of Chemistry Society Faraday Trans 1, vol. 68 (1972) pp. 539-553.

Leszyk, John, et al, "Cross-Linking Of Rabbit Skeletal Muscle Troponin With The Photoactive Reagent 4-Maleimidobenzophenone: Identification Of Residues In Troponin I That Are Close To Cysteine-98 of Troponin C", Biochemistry, vol. 26 (1987) 7042-7047.

Lieberman, K., et al, "A Light Source Smaller Than The Optical Wavelength", Science, vol. 247 (1990) pp. 59-61.

Maruo, Shoji, et al, "Three-Dimensional Microfabrication With Two-Photon-Absorbed Photopolymerization", Optics Letters, vol. 22, No. 2 (1997) pp. 132-134.

Nakamura, O., et al, "A Two-Photon Scanning Fluorescence Microscope With Deep UV Excitation And Near UV Detection", Optik, vol. 100, (1995) pp. 167-170.

Nakamura, O., "Three-Dimensional Imaging Characteristics Of Laser Scan Fluorescence Microscopy: Two-Photon Excitation Vs. Single-Photon Excitation", Optik, vol. 93, (1993) pp. 39-42.

Nakayama, Yasuhide, et al, "Newly Designed Hemostatic Technology Based On Photocurable Gelatin", ASAIO Journal, vol. 41 (1995) pp. M374-M378.

Pan, Hui, et al, "A New Class Of Heterocyclic Compounds For Nonlinear Optics" Chemical Material, vol. 7 (1995) pp. 816-821.

Pitts, Jonathan D., et al., "Submicron Multiphoton Free-Form Fabrication Of Proteins And Ploymers: Studies Of Reaction Efficiencies And Applications In Sustained Release", Macromolecules, vol. 33 (2000) pp. 1514-1523.

Parham, William E., et al, "Synthesis Of Isomeric Methyl Benzoylbenzoates And Substituted o-, m-, and p-Benzoylbenzoic Acids", Journal Organic Chemistry, vol. 39, No. 14, (1974) pp. 2053-2056.

St. John, Pamela M., et al, "Diffraction-Based Cell Detection Using A Microcontact Printed Antibody Grating", Analytical Chemistry, vol. 70, No. 6 (1998) pp. 1108-1111.

Strickler, James H., et al, "Three-Dimensional Optical Data Storage In Refractive Media By Two-Photon Point Excitation", Optics Letters, vol. 16, No. 22 (1991) pp. 1780-1782.

Strickler, James H., et al, "Two-Photon Excitation in Laser Scanning Fluorescence Microscopy", SPIE, vol. 1398, (1990) pp. 107-118.

Sun, Hong-Bo, et al, "Two-Photon Photopolymerization And Diagnosis Of Three-Dimensional Microstructures Containing Fluorescent Dyes", Applied Physics Letters, vol. 79, No. 10 (2001) pp. 1411-1413.

Tao, Terence, et al, "The Conformation Of The C-Terminal Region Of Actin: A Site-Specific Photocrosslinking Study Using Benzophenone-4-maleimide", Archives of Biochemistry And Biophysics, vol. 240, No. 2 (1985) pp. 627-634.

Thayumanavan, S., et al, "Synthesis Of Functionalized Organic Second-Order Nonlinear Optical Chromophores For Electrooptic Applications", Journal of Organic Chemistry, vol. 64 (1999) pp. 4289-4297.

Watanabe, Tsuyoshi, et al, "Development Of High Precision Solid Creation System", RadTech Asia (1993) pp. 462-467.

Weigl, Bernhard H., et al, "Microfluidic Diffusion-Based Separation And Detection", Science, vol. 283 pp. 346-347, Jan. 15, 1999.

Witzgall, George, et al, "Single-Shot Two-Photon Exposure Of Commercial Photoresist For The Production Of Three-Dimensional Structures", Optics Letters, vol. 23, No. 22 (1998) pp. 1745-1747.

Wolfe, John P., et al, "Rational Development Of Practical Catalysts For Aromatic Carbon-Nitrogen Bond Formation", Accounts of Chemical Research, vol. 31, No. 12 (1998) pp. 805-818.

Xia, Younan, et al, "Extending Microcontact Printing As A Microlithographic Technique", Langmuir, vol. 13 (1997) pp. 2059-2067.

* cited by examiner a)

b)

50 microns

PHOTOACTIVATORS, METHODS OF USE, AND THE ARTICLES DERIVED THEREFROM

BACKGROUND

This disclosure relates to photoactivators, in particular photoactivators for use with single- and multi-photon excitation, methods of use of such photoactivators, and the articles derived therefrom.

Tissue engineering is an emerging field because of the unlimited potential to either repair existing tissue or organs or to create them anew. A major challenge in tissue engineering is reproduction of the features of tissues such as skin, muscle, and bone, which are complex, three-dimensional objects on the sub-micrometer scale. Known fabrication techniques such as photolithography and micro-contact printing have severe limitations for tissue engineering because they are not readily amenable to forming three-dimensional structures. Thus, although photolithography can produce features on the 150 nanometer (nm) scale, it is essentially a two-dimensional technique. In addition, photolithographic systems are not water-compatible. Micro-contact printing, or stamping, can produce features on the 500 nm to one micrometer (μm) level, but is also essentially a two-dimensional technique. While some proteins have been stamped, both the available morphologies (essentially two-dimensional) and the reactive chemistries, typically thiols, are quite limited.

Some methods of forming three-dimensional structures in tissue engineering are known, primarily molding-based approaches. These are applicable primarily to synthetic polymers, however, and have a number of drawbacks when applied to naturally occurring molecules such as proteins. Another technique, crosslinking, is also of limited use with naturally occurring molecules, because such molecules are not readily amenable to crosslinking using the currently available chemistries. A two-step crosslinking process for proteins has been reported, using a crosslinking agent comprising a chemically activatable site and a photoactivatable site. In this process the agent is first chemically reacted with a first protein, followed by the photochemical-mediated reaction with a second protein. In addition to the drawback of being a two-step process, like all chemical crosslinking methods this process lacks spatial control and is thus inadequate to reproduce the fine features of real tissues.

One important natural protein is collagen; in fact, the most abundant natural protein is Type 1 collagen. Collagen is a major building block for a wide range of tissues, including skin, muscle, teeth, and bone. Methods to cast or crosslink collagen are known, but the reported methods for casting collagens into three-dimensional shapes are not suitable for providing structural features on the micron and submicron size scale. Collagens are also difficult to crosslink, as known photochemical methods often utilize basic enviroments (pH greater than 7) but most collagens are soluble only in acidic environments. Techniques to assemble proteins such as collagens into three-dimensional structures on a sub-micron scale would be of considerable utility in the fabrication of artificial tissue and other tissue engineering applications. Accordingly, there remains a need in the art for techniques to facilitate crosslinking between proteins such as collagen (type 1 collagen, in particular) to create artificial three-dimensional tissue structures on a sub-micron level. There additionally remains a need for methods of free-form fabrication of two- and three-dimensional tissue structures having dimensions or features in the sub-micron range, especially techniques suitable for synthesis using biomolecular subunits such as proteins, peptides, and oligonucleotides, as well as bioactive small molecules such as hormones, cytokines and drugs.

SUMMARY

The above-described drawbacks and disadvantages are overcome or alleviated by a method for crosslinking a molecule, comprising photoactivating a crosslinker in the presence of the molecule by one-photon or multi-photon excitation, wherein the photactivatable crosslinker comprises at least two photoactivatable chromophores linked by a bridging moiety, and further wherein the point volume of the activation has at least one dimension of less than about 1 micron; and crosslinking the molecule with the activated crosslinker. This method can be advantageously used for crosslinking naturally occurring proteins such as collagens, and provides means for the fabrication of small three-dimensional features, including sub-micron features. It therefore has considerable utility in the fabrication of synthetic biomimetic tissues and engineering scaffolds. Such structures have the potential for excellent biocompatibility with existing tissues and organs.

DETAILED DESCRIPTION

Figure 1:
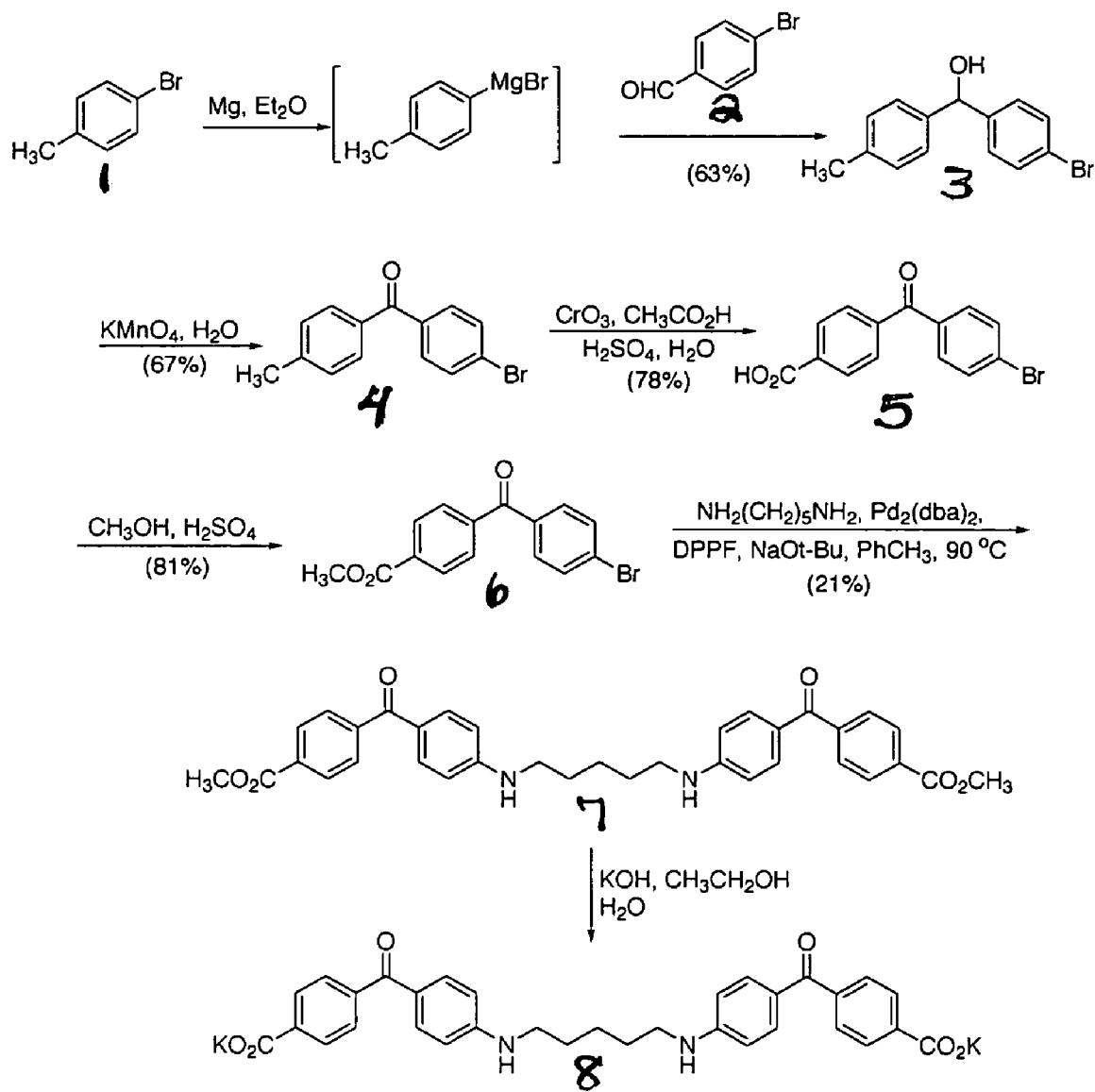
FIG. 1 details the preparation of a benzophenone dimer crosslinking agent.

It has been discovered that certain novel crosslinkers having at least two chromophores that are activated by single- or multi-photon excitation can be advantageously used to connect or to crosslink a wide variety of naturally occurring molecules or their derivatives, and thus can be used to construct two-dimensional or three-dimensional structures on a sub-micron scale. These structures may be used as building blocks for the development or repair of engineered tissues, and have the potential for excellent biocompatibility. Use of visible (400-700 nm), near infrared (700-1000 nm), infrared (1000-3000 nm), or far infrared (3000-10000 nm) illumination minimizes damage to the molecules or portions thereof adjacent to the focal point since many of the naturally-occurring molecules of interest, for example proteins, nucleic acids, lipids, and polysaccharides have minimal absorbance and scattering cross-sections at red and near-infrared wavelengths. Use of two or more photoactivated chromophores on the same molecule further allows greater flexibility in fabrication methods.

Suitable crosslinkers have at least two photoactive groups, i.e., groups that are activatable by single- or multi-photon excitation. Upon absorption of light in the long ultraviolet to far infrared spectral range (250-900 nm), the photoactive groups decompose to form free radicals or otherwise cause the formation of free radicals that initiate crosslinking. Two or more different types of photoactive groups may be present on the same crosslinker. The photoactive groups are covalently attached to a bridging moiety that does not substantially interfere with the photoinitiation or crosslinking reactions. The bridging moiety may further comprise functionalities that moderate the reactivity of the activatable chromophores, or that provide additional reactivity, for example chemical reactivity. The length of the bridging moiety is preferably adjusted to provide the desired reactivity and/or three-dimensional structure.

Suitable photoactive crosslinkers are furthermore substantially water-soluble, which is defined herein as having sufficient solubility in water to provide effective crosslinking upon exposure to single- or multi-photon irradiation. Substantial water solubility enables the crosslinking of naturally occurring biomolecules such as proteins, for example collagen. In general, an effective crosslinker will be at least about 25%, more preferably at least about 50%, still more preferably at least about 75%, and most preferably at least about 90% soluble in water at room temperature. In addition, or alternatively, the photoactive crosslinkers are soluble in an amount of at least about 0.5 millimolar (mM), preferably at least about 1 mM. One method of providing substantial water solubility is to provide the crosslinker with groups that impart water solubility, such as groups that provide hydrogen bonding with water, groups that can form ions, or both. Suitable groups include, but are not limited to, acids and their corresponding salts such as carboxylates, formates, nitrates, phosphates, phosphonates, sulfates, sulfonates, sulfinates, sulfonamides, and the like. Other groups that impart water solubility include organic base groups, such as amines, inorganic base groups, and their corresponding salts. Still other suitable groups that provide strong hydrogen bonding may be used including, for example, hydroxy, phenol, ether, carbonyl, and the like. Preferred metals for the salts are alkali or alkaline earth metals such as sodium, potassium, calcium, and cesium. Metals such as zinc and tin may also be used. The group, e.g., the metal salt, may be attached to one or more chromophores, to the bridging moiety, or both.

Numerous photoactive groups are known, and may be selected without undue experimentation based on the desired activation wavelength, activity, solubility in the reaction medium, availability, and like considerations. Exemplary photoactive groups include, but are not limited to, ketones such as benzophenones, monoketals of alpha-diketones or ketoaldehydes, acyloins and their corresponding ethers, for example benzoin alkyl ethers, 4-aroyl-1,3-dioxolanes, triazines such as chromophore-substituted halomethyl-s-triazines, pyrazines, pyrimidines, pyradizines, oxadiazoles such as chromophore-substituted halomethyl-oxadiazoles, chromophore-substituted disulfides, benzotriazoles, chromophore-substituted azides, phenylglyoxalic esters and derivatives thereof, dimeric phenylglyoxalic esters, peresters, for example benzophenone tetra-carboxylic peresters monoacyl phosphine oxides, for example benzoyldiphenylphosphine oxide, bisacylphosphine oxides, for example bis(benzoyl)phosphine oxide, trisacylphosphine oxides, chalcones, cinnamates, nitrobenzenes, phenyldiazenes, pyridazine diones, phthalazine diones, and the like. To the extent that known photosensitive dyes, for example ethyl eosin, eosin Y, fluorescein, 2,2-dimethoxy-2-phenyl acetophenone, 2-methoxy-2-phenylacetophenone, camphorquinone, rose bengal, methylene blue, erythrosin, phloxime, thionine, riboflavin, methylene green, acridine orange, xanthine dye, and thioxanthine dyes can be covalently linked to a bridging moiety, they may also be used.

The bridging moiety is used to link or tether the photoactive groups, and is generally selected so as to provide a desired crosslink length. Preferably, it does not interfere with the crosslinking reaction, or may to modulate the reactivity of the photoactive groups. Exemplary bridging moieties are divalent, trivalent, tetravalent or higher valency, and may be a hydrocarbon group such as a saturated or unsaturated $C_{1-36}$ alkyl, saturated or unsaturated $C_{3-36}$ cycloalkyl, $C_{6-36}$ aryl, $C_{7-42}$ alkylaryl, or $C_{1-18}$ heterocycle. The bridging moiety may further comprise one or more ionic groups or functional groups such as a halogen, hydroxyl, amino, substituted amino, alkoxy, ether, amide, carboxy ester, phosphate diester, phosphonate diester, sulfate ester, sulfonate ester, sulfhydryl group, or hydrocarbonoxy group comprising one of the foregoing hydrocarbon groups where appropriate.

Further exemplary bridging moieties include but are not limited to polyalkylene glycols such as polyethylene glycol, polyolefins, polybutadienes, polyisoprenes, polyamides, polyesters, polysulfones, polyimides, polyamideimides, polysiloxanes, polyetherimides, polyether sulfones, polyphenylene sulfides, polyether ketones, polyether ether ketones, polystyrenes, polyacrylates, polyacrylonitriles, polyacetals, polycarbonates, polyphenylene ethers, polyurethanes, polyvinylidene chlorides, fluoropolymers, and the like.

Still further exemplary bridging groups include certain divalent biologically active molecules such as certain peptides, oligopeptides, oligonucleotides, saccharides, polysaccharides, fatty acids, lipids, and the like.

The photoactive groups and the bridging moiety may be linked by different types of covalent bonds such as, for example, a carbon-carbon bond, a carbon-nitrogen bond, a carbon-oxygen bond such as an ether, or a carbon-heteroatom bond, including such heterotatoms as sulfur, boron, phosphorus, silicone, and the like. Generally, the linkage will be via a functional group such as such as an amine, amide, imine, urethane, urea sulfide, disulfide, borane, sulfone, phosphate, ether, carboxy ester, sulfonamide, ketone, and the like. Combinations of different linkages may also be used such as, for example, an ester linkage between one photoactive group and the bridging moiety, and an amine linkage between the bridging moiety with the other photoactive group.

Exemplary photoactive crosslinkers may have the structure shown in formula (I)

$$A_1\text{-}L_1\text{-}Q\text{-}L_2\text{-}A_2 \qquad (I)$$

wherein $A_1$ and $A_2$ is the same or different photoactive group, $L_1$ and $L_2$ are linking groups, and Q is a bridging moiety. Exemplary photoactive groups include benzophenones, triazines, benzotriazoles, diazenes, pyridazines, pyrazines, pyrimidines, azides, nitrobenzenes, phthalazine, and the like. An exemplary benzophenone group may have the structure shown in formula (II).

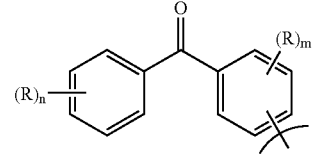

An exemplary triazine group may have the structure shown in formula (III).

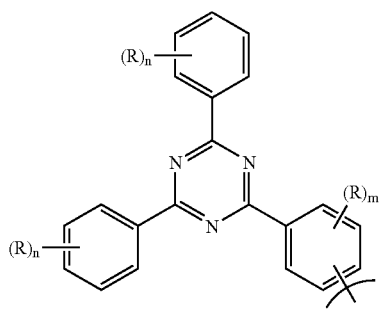
(III)

An exemplary benzotriazole group may have the structure shown in formula (IVa), (IVb), or (IVc).

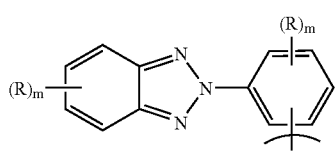
(IVa)

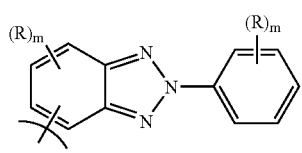
(IVb)

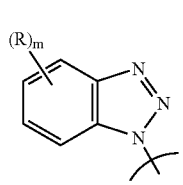
(IVc)

An exemplary diazene group may have the structure —(R)$_m$—N=N—(R)$_m$, in particular the phenyldiazene structure shown in formula (V).

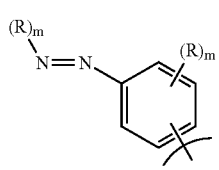
(V)

Exemplary pyridazine, pyrazine, and pyrimidine groups may have the structures shown in formulas (VIa) (VIb), and (VIc), respectively.

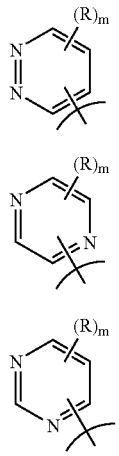
(VIa)
(VIb)
(VIc)

An exemplary azide functionality may have the structure shown in formula (VII).

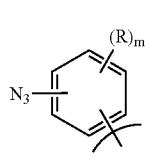
(VII)

An exemplary nitrobenzene functionality may have the structure shown in formula (VIII).

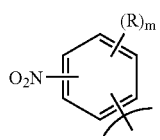
(VIII)

An exemplary pyradazine-3,6-dione may have the structure shown in formula (IX) and and exemplary phthalazine-1,4-dione may have the structure shown in formula (X).

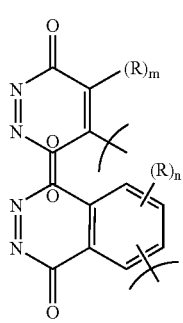
(IX)
(X)

Each R in formulas (II) through (X) may be independently selected from a variety of substituents, including an ionic moiety; a hydrocarbon group such as a saturated or unsaturated, straight or branched chain $C_{1-36}$ alkyl, saturated or unsaturated $C_{3-36}$ cycloalkyl, $C_{6-36}$ aryl, or $C_{7-42}$ alkylaryl; two R groups together may form a fused cyclic or heterocyclic group such as a cycloalkyl or aryl; a functional group such as a halogen, hydroxyl, amino, substituted amino, amide, alkoxy, carboxyl, carboxy ester, phosphate diester, phosphonate diester, sulfate diester, sulfonate diester, sulfhydryl group, or hydrocarbonoxy group comprising one of the foregoing hydrocarbon groups, where appropriate. When R is a hydrocarbon, substituted amino, alkoxy, carboxy ester, sulfate diester, phosphate diester, phosphonate diester, sulfhydryl, or a fused ring, it may further be substituted by the above ionic groups or functional groups. Preferably, R is a $C_{1-18}$ straight chain or branched chain alkyl such as, for example, methyl, ethyl, propyl, isopropyl, butyl, sec-butyl, isobutyl, tert-butyl, pentyl, isopentyl, hexyl, 2-ethylbutyl, 1-methylpentyl, 1,3-dimethylbutyl, heptyl, decyl, or dodecyl; a $C_{3-6}$ alkenyl such, for example, as 2-propenyl, butenyl, 2-butenyl, 3-butenyl, isobutenyl, pentenyl, n-2,4-pentadienyl, hexenyl or 3-methyl-2-butenyl; a $C_{1-18}$ alkoxy such as, for example, the methoxy, ethoxy, propoxy, isopropoxy, n-butoxy, isobutoxy, pentoxy, hexyloxy, octyloxy, decyloxy, dodecyloxy, hexadecyloxy or octadecyloxy; a $C_{3-6}$ alkenoxy; or an aryl such as phenyl, napthenyl or biphenyl. Even more preferably, R is chosen so as to affect the reactivity of the crosslinker, for example by increasing reactivity, shifting the absorption maximum, increasing the multiphoton absorption cross section, or a combination of the foregoing. Thus, for example, two R groups together may form an aryl ring so as to result in the benzophenone group having a napthyl or anthryl substitution. Heteroaromatic substitutions are also within the scope of the invention.

Further in formulas (II), (III) and (IV), n and m are integers that correspond to the number of R groups present in the functionality, and is limited, of course, to a maximum of the valencies available, wherein n is 0 to 5, preferably 1, and m is 0 to 4, preferably 1.

The photoactive crosslinkers as described above may be used to crosslink a variety of water-soluble molecules useful in tissue engineering, wherein such molecules are soluble in acidic, basic, or neutral aqueous solutions. Aqueous solutions as used herein includes solutions comprising miscible non-aqueous solvents such as methanol, ethanol, or acetone, in amounts of up to about 20 percent by volume. Crosslinking may occur within a single molecule and/or between two molecules. Suitable molecules include amino acids, peptides, oligopeptides, and proteins, including enzymes, myosin, collagen, and the like; fatty acids and lipids; ribonucleic acids, deoxyribonucleic acids, and oligomers and polymers thereof; and saccharides, polysaccharides, glycosaminoglycans, and mixtures comprising at least one of the foregoing molecules. Various bioactive agents such as cytokines, hormones, receptors, growth factors, and drugs; optically active synthetic agents (including inorganic compounds); and optically active biocompounds such as caged compounds and fluorophores may also be crosslinked. These molecules are not readily amenable to existing methods of nanofabrication, as they are often only sensitive to UV light, and must be reacted in solution, problems which are solved by the present method. Derivatized and synthetic variations of the foregoing molecules may also be used, as well as plant-derived materials such as cellulose.

Other molecules may be added to the reactive environment to facilitate the reaction, so long as these molecules do not substantially interfere with the crosslinking reactions, and in particular are transparent to the radiation used for crosslinking. Substantial transparency allows more precise focus of the laser beam, and minimization of unwanted side reactions. The molecules may be in solution, preferably aqueous solution, adsorbed to a substrate, or in suspension or emulsion. Any solvent must also be substantially transparent to the radiation used to fabricate the structures.

As stated above, small two- or three-dimensional structures may be formed by single or multiple photon-induced cross-linking of a molecule such collagen with the photoactive crosslinker. Nonlinear optics are presently preferred in the process. There are a number of advantages to the use of nonlinear optics in freeform fabrication, one of the most important being that it allows for high-energy peak power to be confined to a smaller area than that achievable with linear infrared optics. Practical realization of two-photon laser scanning microscopy is described by W. Denk, J. H. Strickler, and W. W. Webb in Science, Vol. 248, p. 73 (1990), which is incorporated herein by reference. Other uses and descriptions of two-photon excitation are further described by O. Nakamura in Optik, Vol. 93, p. 39 et seq. (1993); by O. Nakamura and T. Okada in Optik, Vol. 100, p. 167 et seq. (1995); by E. S. Wu, J. H. Strickler, W. R. Harrell, and W. W. Webb in Proc. SPIE, Vol. 1398, p. 107 et seq. (1990) and in U.S. Pat. No. 5,289,407 to Strickler and Webb; and by Watanabe, M. Okawa, T. Ukachi, F. Kurihara, and H. Harimaya, In Proceedings of RadTech Asia 1993, p. 462, published by RadTech, Japan (1993), the relevant portions of which preceding references are also incorporated by reference herein. A Light Source Smaller Than the Optical Wavelength by K. Liebermann, S. Harush, A. Lewis, and R. Kopelman, Science, Vol. 247, pp. 61 (1990) is further incorporated by reference herein.

The method is particularly suitable for the formation of three-dimensional objects or structures having dimensions on the micro- and nanometer scale, that is, structures built up from elements with point volumes having dimensions of less than about 1 micron, preferably elements having at least one dimension of less than about 500 nm, 250 nm, 100 nm, and most preferably less than about 50 nm. In preferred embodiments, use of two-photon wide field (far field) excitation allows the formation of structures comprising individual point volumes with X-Y dimensions of less than about 300 nm and optionally a Z dimension of less than about 500 nm, while use of three-photon far field excitation allows the formation of structures comprising individual point volumes with X-Y dimensions of less than about 250 nm and optionally a Z dimension of less than about 300 nm.

Single- or multi-photon excitation/activation of the photoactive crosslinker may be undertaken using deep red, red, infrared, and other visible light optics. Lasers operated at these wavelengths also provide for diffraction limited light sources. Additionally, fiber optics may be easily used for light transmission, resulting in higher energy, less beam spread, better collimation, and less chromatic spread compared to using UV-associated optics.

The photoactive crosslinkers may be used to fabricate structures in situ and below surfaces in a wide variety of applications, particularly medical and dental applications. Some examples where the photoactive crosslinkers may be used in conjunction with multi-photon excitation include delivering biologically active compounds such as antisense oligonucleotides, anti-angiogenesis compounds, hormones, or antibacterial agents, growth factors, or cytotoxins directly into or onto a site of action, for example diseased or damaged tissue or tumors. The photoactive crosslinkers may also be used for controlled delivery of tissue engineering scaffold agents, growth factors, and cells for a variety of purposes, for example to assemble scaffolds in situ to restore, effect repairs, or strengthen tendon and ligament attachment, to facilitate wound healing, for example in chronic sores, to provide a matrix for chrondorcytes growth in damaged articular cartilage, or for site directed repair and rebuilding of anuretic or hemorrhagic arteries via minimally invasive reconstruction, for example repair of arterial walls following angioplasty or other trauma, and to provide minimally invasive assembly of structural elements or devices such as stents.

Other exemplary uses include fabrication of matrices in or on the gingiva, for example to effect photooptical fabrication directly in the sulcus space, to deliver and/or attach therapeutic agents to diseased and damaged gingival and other epithelial lesions; and for in situ photodynamic therapy, as disclosed, for example, by J. Bhawalkar and N. Kumar et al. in Two-Photon Photodynamic Therapy, Journal of Clinical Laser Medicine & Surgery, Vol. 15, pp. 201-204(1997). Other uses include the creation of protein-based structures for non-tissue engineering applications, including but not limited to biosensors, environmental sensors, drug testing, and living computers. The above-described embodiments may also be combined as desired in order to create complex devices and structures. For example, devices with a combination of enzymes, motile proteins, and optical properties may be used for biosensor applications. Fiber optic fabrication systems may be used for catheter-driven repair of tissue damage or to deliver biodegradable compounds to effect tumor killing.

A number of advantages result from the use of multi-photon excitation for reaction of the photoactive crosslinkers. Because of the ability of multi-photon excitation to probe deeply into a bulk or solution phase sample with an unprecedented degree of control in the x- and y-, as well as z-directions, with only minimal optical effects above and below the focal point, proteins can be accurately and precisely connected with reactive sites on naturally occurring tissues. Additionally, the use of multi-photon excitation allows synthesis with various photoactive molecules, in that infrared, red, deep red, and visible light illumination minimizes damage to proteins, enzymes, or organic molecules adjacent to the focal point, due to the minimal absorbance and scattering of IR and red light compared to UV light. Use of IR and red light also permits fabrication within tissues and through turbid media such as blood. A further advantage is that it is possible to limit the size of a fabricated feature to an area even smaller than the focal point of the photon source, by focusing the activation zone (the area of high proton density) partially within a non-reactive substrate or other location where activation does not occur.

The invention is further illustrated by the following non-limiting examples.

The procedure below details the synthesis of a benzophenone dimer comprising a metal carboxylate and linked by a diamine terminated bridging moiety via the scheme set forth in FIG. 1. As shown in FIG. 1, synthesis of the benzophenone crosslinker (8) starts with a reaction between a Grignard reagent derived from commercially available 4-bromotoluene (1) and 4-bromobenzaldehyde (2), yielding (4'-bromophenyl)-4-methylphenyl methanol (3). Alcohol (3) was then oxidized with potassium permanganate ($KMnO_4$) to provide 4-bromophenyl-p-toylmethanone (4), followed by oxidation of the methyl group with $CrO_3$ to yield 4-(p-bromobenzoyl) benzoic acid (5). Esterification of acid (5) provided 4-(p-bromobenzoyl) benzoate (6). The bifunctional coupling between pentane diamine ($NH_2(CH_2)_5NH_2$) and methyl 4-(p-bromobenzoyl) benzoate (6) to yield the benzophenone dimer (7) was achieved using 1,1-bis(diphenylphosphino)ferrocene (DPPF) as the catalyst. The benzophenone dimer (7) was then hydrolyzed to provide the dipotassium salt (8). Details of each step are set forth below.

Preparation of (4'-bromophenyl)-4-methylphenyl methanol (3)

Magnesium turnings (0.39 g, 0.016 mol) were dried in a flask and then cooled under nitrogen. Anhydrous diethyl ether (3 mL) was added, followed by 4-bromotoluene (3.0 g, 1.8 mmol). The mixture was refluxed, and more anhydrous diethyl ether was added to keep the solution volume constant. The resultant Grignard solution was added dropwise to a solution of 4-bromobenzaldehyde (1.66 g, 9.0 mmol) in anhydrous diethyl ether(6 mL). The reaction was heated with reflux for 30 minutes, following which it was cooled. The cooled solution was poured into a solution of hydrochloric acid (HCl) (3.7 milliliters (mL) concentrated HCl in 17 grams of ice-water) and stirred for 1 hour (h). The resulting mixture was extracted with diethyl ether (3 times, 50 mL each), and the combined organic extracts were dried using magnesium sulfate ($MgSO_4$) and concentrated in vacuo. Purification by flash chromatography on silica gel (petroleum ether/ethyl acetate, 90/10, v/v) afforded 1.53 grams of (4'-bromophenyl)-4-methylphenyl methanol, a yield of about 62% as a white solid. The melting point (mp) was 80-81° C.

Preparation of 4-bromophenyl-p-toylmethanone (4)

A solution of (4'-bromophenyl)-4-methylphenyl methanol (3) (1.04 g, 3.8 mmol), $KMnO_4$ (1.56 g, 9.9 mmol) and water (18 mL) was refluxed for 5 h. The reaction mixture was cooled and then acidified to a pH of 2 with concentrated HCl. The mixture was filtered and the filtrate extracted with diethyl ether (3 times, 50 mL each). The combined organic extracts were dried using $MgSO_4$, filtered and concentrated. Purification by flash chromatography on silica gel (petroleum ether/ethyl acetate, 90/10, v/v) afforded 0.68 g of 4-bromophenyl-p-toylmethanone; a yield of 67% as a white solid. The melting point was 138-139° C.

Preparation of 4-(p-bromobenzoyl) benzoic acid (5)

4-bromobenzoyl-p-toylmethanone (4) (1.75 g, 6.4 mmol) dissolved in warm acetic acid (6.55 mol) was kept just below the boiling point. A solution of chromic acid (1.73 g. 0.0173 mol) in water ($H_2O$) (3.95 mL), acetic acid (6.43 mL) and concentrated sulfuric acid (1.24 mL) was added slowly to the solution. The reaction was monitored by thin liquid chromatography (TLC) until the starting material was consumed. The reaction mixture was then filtered, and the solid was rinsed with water. The white residue was purified by flash chromatography on silica gel (ethyl acetate/acetic acid, 99.5/0.5, v/v) to give 1.36 grams of 4-(p-bromobenzoyl) benzoic acid; a yield of 78% as a white solid. The melting point was 270-271° C.

Preparation of methyl 4-(p-bromobenzoyl) benzoate (6)

4-(p-bromobenzoyl) benzoic acid (5) (0.20 g, 0.66 mmol) was added to a solution of methanol (2 mL) and concentrated sulfuric acid (0.23 mL) and stirred under reflux. The reaction was monitored by thin layer chromatography (TLC) until the acid was consumed. The resulting solution was concentrated in vacuo. Purification by flash chromatography on silica gel (petroleum ether/ethyl acetate, 90/10, v/v) afforded 0.16 grams of methyl 4-(p-bromobenzoyl) benzoate; a yield of 81%. The methyl 4-(p-bromobenzoyl) benzoate is a slightly pink solid with a melting point of 177-178° C.

Preparation of Benzophenone Dimer (7)

A dried Schlenk tube was charged with methyl 4-(p-bromobenzoyl) benzoate (6) (0.20 g, 0.63 mmol), tris (dibenzylidene acetone) dipalladium (0.029 g, 0.032 mmol), DPPF (0.035 g, 0.063 mmol) and toluene (8 mL) under nitrogen. The reaction was capped with a polytetrafluoroethylene (PTFE) septum, and pentanediamine (0.026 g, 0.252 mmol) was added via syringe. The reaction mixture was then heated to 90° C. for 12 hours. The cooled mixture was diluted with diethyl ether (30 mL) and then concentrated in vacuo. Purification by flash chromatography on silica gel (petroleum ether/ethyl acetate, 50/50, v/v) afforded 0.072 grams (a yield of 21%) as a pale yellow solid:

Preparation of Dipotassium Salt (8)

A solution of benzophenone dimer (7) (0.030 g, 0.052 mmol) and potassium hydroxide (0.005 g, 0.10 mmol) in ethanol (3 mL)/water (0.16 mL) was stirred at room temperature for 2.5 hours. The solvents were removed by freeze-drying, and the residue was triturated with diethyl ether. The dimer as the potassium salt was isolated as a pale yellow solid. The yield was 63%.

The fabrication apparatus for the multi-photon excitation consisted of a laser scanning confocal microscope commercially available as Biorad MRC600, and Axioscope upright microscope stand modified for near-infrared excitation with a femto-second titanium sapphire oscillator commercially available as 900-F from Coherent. The laser was operated between 780 and 850 nanometers (nm) with a repetition rate of 76 Megahertz (MHz) at 100 femto-second pulse duration with an average power to the sample of approximately 50 milli-watts (mW) or about 1 nano-joule (nJ) per pulse. With a 0.75 numerical aperture (NA) lens this corresponds to a peak power of roughly $10^{10}$ watts/square centimeter ($W/cm^2$). The laser scanner is configured to perform line and rectangular raster scans, where the latter scan consists of 768×512 pixels, which for a 20× lens (lens having a magnification of 20) yields a full field of view of 670 by 447 micrometers. Pixel dwell times are 1.6 micro-seconds (µs), or about 50 laser pulses per pixel. Optical diagnostics are measured via either two-photon excited fluorescence arising from the photoactivator (confocal detection), or via the transmitted light. Line scans were repetitively performed until polymerization was observed via the appearance of a change in refractive index. While not rigorously quantitative, this method is suitable for comparison of changes in polymerization efficiency and the results were consistent between different sets of experiments.

The absorption and emission spectra were measured using spectrometers commercially available from Varian and/or Spex. Power dependency measurements to determine if the excitation of the benzophenone dimer occurred via two or three photon absorption were performed by monitoring the relative fluorescence intensities. These determinations were performed at 780, 810, and 847 nm by an epi-illumination fluorescence setup. A 0.25 N.A., 5× objective from Zeiss was used for the excitation and fluorescence collection detected at 90 degrees from the incident light. The laser power was attenuated with a λ/2 plate (i.e. a half wavelength retarder) and a Glan Laser polarizer commercially available from CVI Laser and others. The fluorescence was separated with a long wave pass dichroic (550 nm commercially available from, CVI Laser and the residual laser was blocked by BG-39 color glass filters. The filtered signal was detected by a PMT commercially available as R4632 from Hamamatsu, pre-amplified using a Stanford Research Systems SR350, and boxcar averaged using a Stanford Research Systems SR250.

Figure 2:
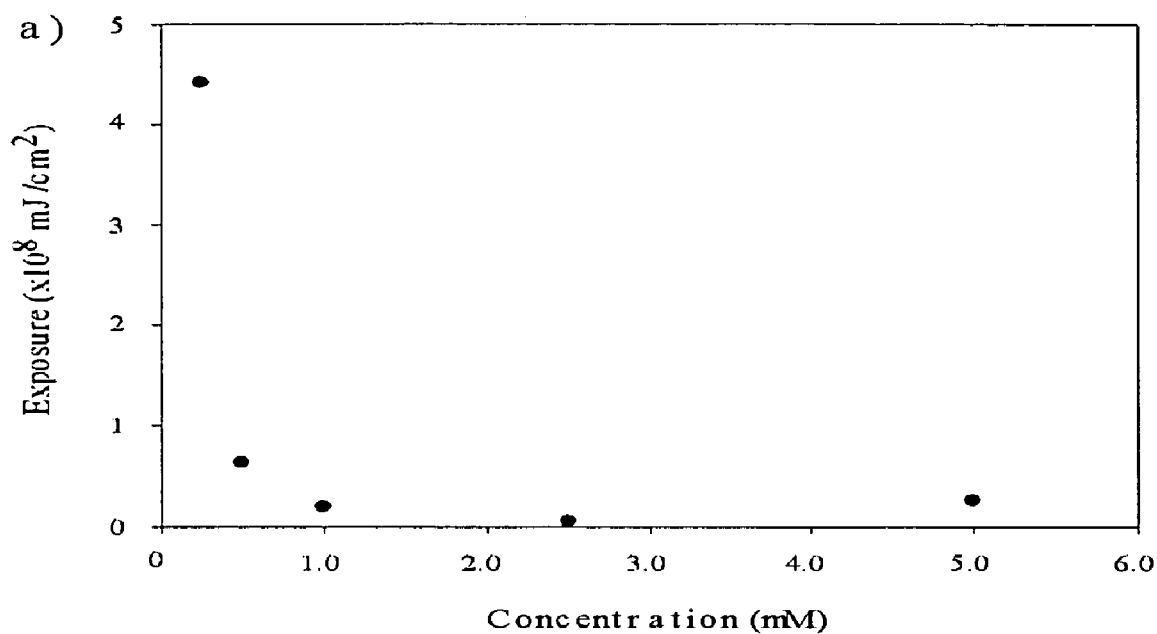
FIG. 2 is a graph illustrating that the cross-linking efficiency of a benzophenone dimer with bovine serum albumen is dependent upon the concentration of the benzophenone dimer.

The potassium salt of benzophenone dimer (8) was next used to crosslink either bovine serum albumen or type 1 collagen using multi-photon excitation. FIG. 2 shows that the cross-linking efficiency of benzophenone dimer (8) with bovine serum albumen is based on the concentration of the salt of the dimer. Repetitive line scans were run until the onset of cross-linking was determined by a visible change in refractive index. The efficiency is measured in terms of integrated light flux $mJ/cm^2$. It was observed that the benzophenone dimer (8) displays a strong concentration dependence on the reaction efficiency, indicating that it is either being degraded or becoming incorporated into the matrix.

Figure 3:
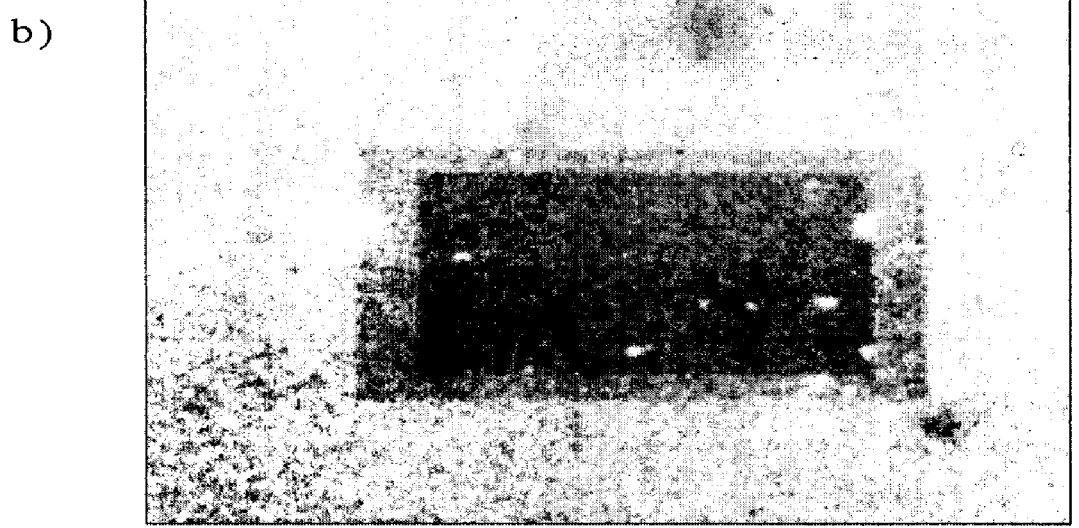
FIG. 3 is a light microscope image with the contrast arising from the change in refractive index when a benzophenone dimer is reacted with type 1 collagen to form a rectangular matrix in three dimensions.

FIG. 3 is a micrograph showing the result of the reaction of the salt of the benzophenone dimer (8) with type 1 collagen. The contrast in the image arises from the change in refractive index, as well as residual fluorescence from the benzophenone dimer. This structure was a two-tiered rectangle of type 1 collagen, starting from a freely diffusing mixture of collagen and photoactivator in a sealed sample chamber. Using the microscope the glass support was located at the focus, and the molecules were pulled from solution down to the support to form the first layer. During the experiment, the focal plane of the source of multi-photon excitation was lowered and a smaller layer was cross-linked on top. In general, either the fosuing optic or the sample can be moved with respect to each other, here the sample moved and the optics were held fixed. The bottom layer was approximately 135×95 microns and each layer was approximately 4 microns in height. Thus a 3-dimensional structure was formed. This 3-dimensional structure was adherent to the glass substrate and had long-term stability (at least several hours after fabrication).

The photoactive crosslinkers having two photo-activated sites have number of advantages over the existing bifunctional activators, which have one photochemical site and one chemical site. These photoactive molecules can simultaneously link two proteins together thereby providing greater flexibility in fabricating artificial tissues or repairing damaged tissues. The method of using multi-photon excitation when combined with the photoactive molecules also reduces the time to perform such operations when compared with those methods utilizing chemical conjugation.

The use of the photoactive molecule to connect naturally occurring molecules in real tissues is a significant advance in tissue engineering, since collagen is present (and often the major component) in a great number of different tissues. As stated above, current scaffolding technologies have little or no spatial control of the crosslinks. This can only be accomplished photochemically, since a laser can be directed to form desired shapes and sizes. The use of multi-photon excitation increases the spatial control from two to three dimensions. The benzophenone dimer shown in the example above is especially efficient in photocrosslinking collagen. Due to its low solubility in aqueous media, collagen is especially difficult to photocrosslink by existing chemistries.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention.

What is claimed is:

1. A method for crosslinking one or more molecules, comprising
    photoactivating a photactivatable crosslinker in the presence of the one or more molecules by multi-photon excitation, wherein the crosslinker comprises at least two photoactive groups covalently linked by a bridging moiety, and further wherein the point volume of the activation produces a structural element that has at least one dimension of less than about 1 micron; and
    crosslinking the one or more molecules with the activated crosslinker,
    wherein the crosslinking produces a three-dimensional structure,
    wherein the photoactive groups are selected from the group consisting of benzophenones, triazines, chromophore-substituted halomethyl-s-triazines, pyrazines, pyrimidines, pyradizines, benzotriazoles, nitrobenzenes, phenyldiazenes, pyridazine diones, phthalazine diones, and a combination comprising at least one of the foregoing photoactive groups.

2. The method of claim 1, wherein the photoactivatable crosslinker is substantially water-soluble.

3. The method of claim 2, wherein the photoactivatable crosslinker comprises at least one acid or acid salt.

4. The method of claim 3, wherein the acid salt is the alkali or alkaline earth metal salt of a carboxylate, formate, nitrate, phosphate, phosphonate, phosphinate, sulfate, or sulfonate.

5. The method of claim 2, wherein the photoactivatable crosslinker comprises at least one base or base salt.

6. The method of claim 2, wherein the photoactivatable crosslinker comprises at least one group capable of hydrogen bonding with water.

7. The method of claim 1, wherein the photoactivatable crosslinker has the structure (I)

(I)

wherein $A_1$ and $A_2$ are the same or different photoactive groups, wherein $A_1$ and $A_2$ are selected from the group consisting of

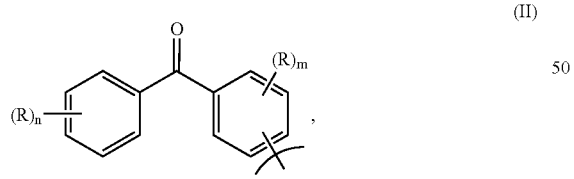
(II)

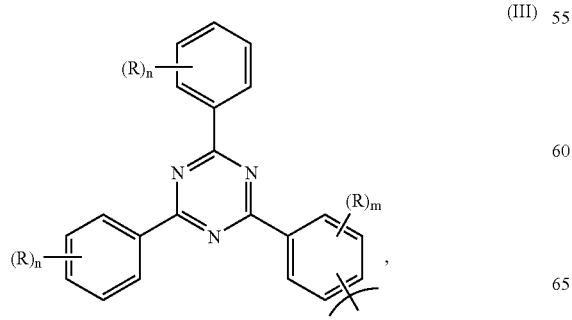
(III)

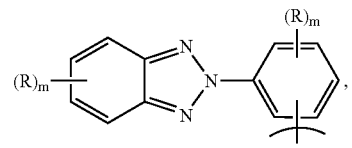
(IVa)

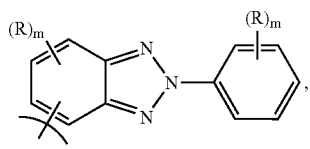
(IVb)

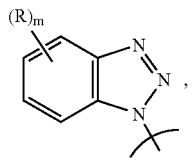
(IVc)

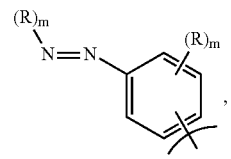
(V)

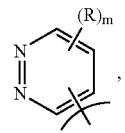
(VIa)

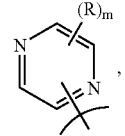
(VIb)

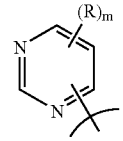
(VIc)

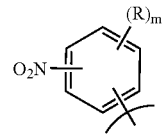
(VIII)

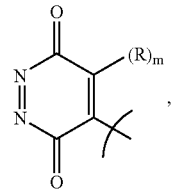
(IX)

-continued

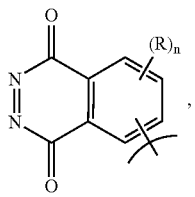

(X)

and a combination of these photoactive groups, wherein
each R in the formulas are independently selected from an ionic moiety; a saturated or unsaturated, substituted or unsubstituted $C_{1-36}$ alkyl, saturated or unsaturated, substituted or unsubstituted $C_{3-36}$ cycloalkyl, substituted or unsubstituted $C_{6-36}$ aryl, or substituted or unsubstituted $C_{7-42}$ alkylaryl; two R groups together may form a fused cyclic or heterocyclic group such as a cycloalkyl or aryl; a halogen, hydroxyl, amino, substituted amino, amide, alkoxy, carboxyl, carboxy ester, phosphate ester, phosphonate ester, sulfate ester, sulfonate ester, sulfhychyl group, or hydrocarbonoxy group optionally comprising one of the foregoing hydrocarbon groups
n is 0 to 5 and m is 0 to 4;

$L_1$ and $L_2$ are linking groups; and

Q is a bridging moiety.

8. The method of claim 7, wherein the bridging moiety is a divalent, saturated or unsaturated, substituted or unsubstituted $C_{1-36}$ alkyl, saturated or unsaturated, substituted or unsubstituted $C_{3-36}$ cycloalicyl, saturated or unsaturated, substituted or unsubstituted $C_{3-36}$ methylcycloalkyl, $C_{6-36}$ aryl, $C_{7-42}$ alkylaiyl, $C_{7-42}$ aralkyl, $C_{1-18}$ heterocycle, a polyaWylene glycol, polyolefin, polybutadiene, polyisoprene, polyamide, polyester, polysulfone, polyimide, polyamideimide, polysiloxane, polyetherimide, polyether sulfone, polyphenylene sulfide, polyether ketone, polyether ether ketone, polystyrene, polyacrylate, polyaciylonitrile, polyacetal, polycarbonate, polyphenylene ether, polyurethane, polyvinylidene chloride, fluoropolymer, peptide, oligopeptide, oligonucleotide, saccharide, polysaccharide, fatty acid, or lipid.

9. The method of claim 7, wherein the photoactivatable crosslinker comprise an acid or acid salt.

10. The method of claim 1, wherein the molecule is an amino acid, peptide, oligopeptide, protein, enzyme, myosin, collagen, fatty acid, lipid, ribonucleic acid, deoxyribonucleic acid, oligomer, saccharide, polysaccharide, glycosaminoglycan, cellulose, cytokine, hormone, receptor, growth factor, drug or a mixture comprising at least one of the foregoing molecules.

11. A product derived by the method of claim 1.

12. A method for crosslinking one or more molecules, comprising
photoactivating a photactivatable crosslinker in the presence of the one or more molecules by multi-photon excitation, wherein the crosslinker comprises at least two photoactive groups covalently linked by a bridging moiety, and further wherein the point volume of the activation produces a structural element that has at least one dimension of less than about 1 micron; and
crosslinking the one or more molecules with the activated crosslinker, wherein the crosslinking produces a three-dimensional structure built up from elements with point volumes having at least one dimension of less than about 1 micron; and wherein the photoactivatable crosslinker has the structure (I)

$$A_1\text{-}L_1\text{-}Q\text{-}L_2\text{-}A_2 \qquad (I)$$

wherein $A_1$ and $A_2$ are the same or different photoactive groups, wherein $A_1$ and $A_2$ are selected from the group consisting of

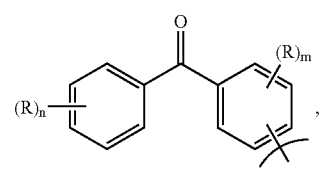

(II)

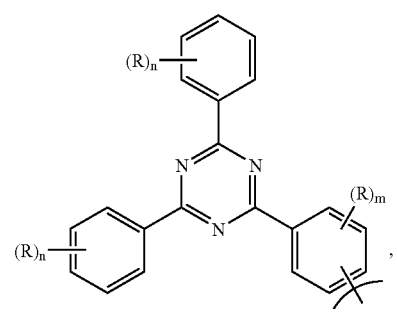

(III)

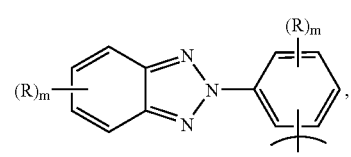

(IVa)

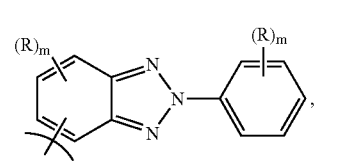

(IVb)

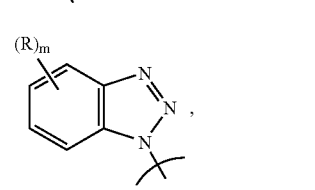

(IVc)

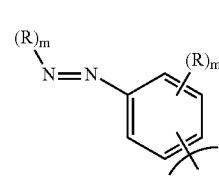

(V)

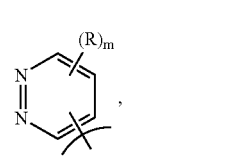

(VIa)

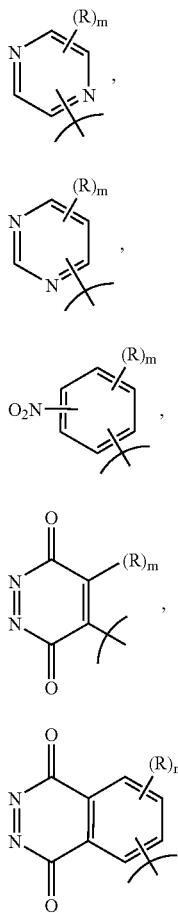

and a combination of these photoactive groups, wherein each R in the formulas are independently selected from an ionic moiety; a saturated or unsaturated, substituted or unsubstituted $C_{1-36}$ alkyl, saturated or unsaturated, substituted or unsubstituted $C_{3-36}$ cycloalkyl, substituted or unsubstituted $C_{6-36}$ aryl, or substituted or unsubstituted $C_{7-42}$ alkylaryl; two R groups together may form a fused cyclic or heterocyclic group such as a cycloalkyl or aryl; a halogen, hydroxyl, amino, substituted amino, amide, alkoxy, carboxyl, carboxy ester, phosphate ester, phosphonate ester, sulfate ester, sulfonate ester, sulfhydryl group, or hydrocarbonoxy group optionally comprising one of the foregoing hydrocarbon groups n is 0 to 5 and m is 0 to 4;

$L_1$ and $L_2$ are linking groups; and

Q is a bridging moiety.

13. The method of claim 12, wherein the bridging moiety is a divalent, saturated or unsaturated, substituted or unsubstituted $C_{1-36}$ alkyl, saturated or unsaturated, substituted or unsubstituted $C_{3-36}$ cycloalkyl, saturated or unsaturated, substituted or unsubstituted $C_{3-36}$ methylcycloallcyl, $C_{6-36}$ aryl, $C_{7-42}$ alkylaiyl, $C_{7-42}$ aralkyl, $C_{1-18}$ heterocycle, a polyalkylene glycol, polyolefin, polybutadiene, polyisoprene, polyamide, polyester, polysulfone, polyimide, polyamide-imide, polysiloxane, polyetherimide, polyether sulfone, polyphenylene sulfide, polyether ketone, polyether ether ketone, polystyrene, polyacrylate, polyacrylonitrile, polyacetal, polycarbonate, polyphenylene ether, polyurethane, polyvinylidene chloride, fluoropolymer, peptide, oligopeptide, oligonucleotide, saccharide, polysaccharide, fatty acid, or lipid.

14. The method of claim 12, wherein the photoactivatable crosslinker comprise an acid or acid salt.

15. The method of claim 12, wherein the molecule is an amino acid, peptide, oligopeptide, protein, enzyme, myosin, collagen, fatty acid, lipid, ribonucleic acid, deoxyribonucleic acid, oligomer, saccharide, polysaccharide, glycosaminoglycan, cellulose, cytokine, hormone, receptor, growth factor, drug or a mixture comprising at least one of the foregoing molecules.

* * * * *